(12) United States Patent
Maitra et al.

(10) Patent No.: US 8,133,478 B2
(45) Date of Patent: Mar. 13, 2012

(54) COSMETIC NANOCOMPOSITES BASED ON IN-SITU CROSS-LINKED POSS MATERIALS

(75) Inventors: Prithwiraj Maitra, Randolph, NJ (US); Tao Zheng, Nanuet, NY (US)

(73) Assignee: Avon Products Inc., New York, NY (US)

( * ) Notice: Subject to any disclaimer, the term of this patent is extended or adjusted under 35 U.S.C. 154(b) by 1255 days.

(21) Appl. No.: 11/801,287

(22) Filed: May 9, 2007

(65) Prior Publication Data

US 2008/0279797 A1    Nov. 13, 2008

(51) Int. Cl.
*A61Q 1/04* (2006.01)
*A61Q 1/08* (2006.01)
*A61Q 1/10* (2006.01)
*A61Q 5/02* (2006.01)
*A61Q 5/12* (2006.01)
*A61Q 17/02* (2006.01)
*A61Q 17/04* (2006.01)

(52) U.S. Cl. ............. 424/64; 424/59; 424/69; 424/70.1; 424/70.121; 424/70.7; 424/78.03; 424/401; 424/405

(58) Field of Classification Search .................. None
See application file for complete search history.

(56) References Cited

U.S. PATENT DOCUMENTS

| | | | |
|---|---|---|---|
| 326,606 A | 9/1885 | Tingley | |
| 449,224 A | 3/1891 | Long | |
| 3,159,601 A | 12/1964 | Ashby | |
| 3,159,662 A | 12/1964 | Ashby | |
| 3,220,972 A | 11/1965 | Lamoreaux | |
| 3,445,420 A | 5/1969 | Kookootsedes et al. | |
| 3,516,946 A | 6/1970 | Modic | |
| 3,576,027 A | 4/1971 | Fish | |
| 3,715,334 A | 2/1973 | Karstedt | |
| 3,757,782 A | 9/1973 | Aiken | |
| 3,775,452 A | 11/1973 | Karstedt | |
| 3,814,730 A | 6/1974 | Karstedt | |
| 4,196,808 A | 4/1980 | Pardo | |
| 4,256,870 A | 3/1981 | Eckberg | |
| 4,465,818 A | 8/1984 | Shirahata et al. | |
| 4,562,096 A | 12/1985 | Lo et al. | |
| 4,681,963 A | 7/1987 | Lewis | |
| 5,318,203 A | 6/1994 | Iaia et al. | |
| 5,629,387 A | 5/1997 | Frances et al. | |
| 5,789,334 A | 8/1998 | Nakanishi et al. | |
| 5,942,638 A | 8/1999 | Lichtenhan et al. | |
| 6,074,654 A | 6/2000 | Drechsler et al. | |
| 6,247,586 B1 | 6/2001 | Herzog et al. | |
| 6,303,728 B1 | 10/2001 | Hagimori et al. | |
| 6,307,082 B1 | 10/2001 | Klein et al. | |
| 6,789,971 B2 | 9/2004 | Tsaur | |
| 2004/0120915 A1 | 6/2004 | Yang et al. | |
| 2004/0165935 A1 | 8/2004 | Kauffmann et al. | |
| 2004/0202622 A1 | 10/2004 | Quadir | |
| 2004/0202623 A1 | 10/2004 | Quadir | |
| 2005/0000531 A1 | 1/2005 | Shi | |
| 2005/0276779 A1* | 12/2005 | Blin | 424/70.16 |
| 2007/0224141 A1* | 9/2007 | Themens et al. | 424/63 |

FOREIGN PATENT DOCUMENTS

| WO | WO 2004/082611 A2 | 9/2004 |
|---|---|---|
| WO | WO 2006/031781 A1 | 3/2006 |

* cited by examiner

*Primary Examiner* — Jyothsna Venkat
(74) *Attorney, Agent, or Firm* — Joan M. McGillycuddy; Charles J. Zeller (57) ABSTRACT

A cosmetic composition for caring for and/or making up the skin, lips and/or body in the form of a film, which is non-transferable, long-lasting with a comfortable feeling of use to consumers over long periods of wear time. The composition contains graftable POSS which forms a film when it cures in situ. The invention also relates to using such film for preparing a cosmetic composition and a makeup process and makeup kit comprising the product.

10 Claims, 4 Drawing Sheets

R = H, OSiMe$_2$R, vinyl, epoxide, methacruylate, NH$_2$, LC mesogens, etc. [4-8]

FIG. 1

FIG. 2 where R = and M is equal to from about 1500 to about 4500.

COSMETIC NANOCOMPOSITES BASED ON IN-SITU CROSS-LINKED POSS MATERIALS

FIELD OF THE INVENTION

The present invention relates to compositions and methods of forming films in situ on mammalian keratinous tissues and particularly, use of graftable Polyhedral Oligo Silsequioxanes (POSS) in a topical cosmetic composition for application to the skin or lips.

BACKGROUND OF THE INVENTION

Many cosmetic compositions attempt to provide transfer resistance and sustainability to prevent the inconvenience of having to reapply product in order to restore or refresh the desired appearance. Further, the mobility of some cosmetic compositions allows the product to migrate and concentrate into the fine lines, wrinkles, folds or pores of the skin or lips either accentuating wrinkles or resulting in an undesirable non-uniform appearance. Other products interact with sebum or sweat, or in the case of lipsticks, saliva, resulting in poor product sustainability.

There remains a technology gap in providing a non-transfer, long-lasting cosmetic composition, which is also comfortable to consumers over long periods of wear time. Current products in the market either deliver one or two of these attributes but fail to deliver on all; namely long lasting non-transfer products are available but are very uncomfortable and taut on the skin or lips. Although a variety of synthetic as well as natural polymers and high melting point wax ingredients, or hydrophobic resins have been investigated and used in products previously, they fail to deliver on all four attributes of non-transfer, long-wear, breathable, and comfortable. Other products include water-soluble film-formers or emulsion compositions.

Compositions have also been proposed which allow a film to be applied to the skin. Cosmetic films must exhibit some degree of plasticity. Most often, synthetic polymers are incorporated into cosmetic compositions to form the cosmetic film. However, this results in rigid films which are brittle, and uncomfortable. Additionally, the water soluble ingredients are easily rubbed off or removed under such conditions as sweating, washing, swimming, eating or drinking.

Several patent applications disclose cosmetic compositions containing Polyhedral Oligo Silsequioxane (POSS) or extended Polyhedral Oligo Silsequioxane (EPOSS) molecules containing six or more Si atoms within their cage-like structure. POSS or EPOSS is utilized as physical fillers in the cosmetic composition or grafted to acrylic polymer to provide UV protection. These applications do not disclose in-situ cross-linking.

Patent Application WO 2006/031781 discloses a cosmetic composition with POSS and non-POSS silicone resin, having repeating nonfunctional or $R_3SiO_{0.5}$ "M" units and the quadfunctional or $SiO_2$ "Q" units, known as MQ resins. POSS is used as a physical filler in the cosmetic composition. This application does not disclose in-situ cross-linking.

Patent Application No. US 2004/0120915, US 2004/0202623, WO 2004/082611, US 20040202622 discloses a variety of POSS molecules for application in cleanser and home personal care applications. POSS is used for UV protection and as a delivery system. This application does not disclose in-situ cross-linking.

Two-step lip color systems which are long-lasting provide a pigmented base coat for color and wear and a secondary top coat for gloss and lubricity. These products may wear off unevenly over time resulting in undesirable appearance and do not always have sufficient staying power. They may also feel dry, tight, and uncomfortable, and may appear matte.

Therefore, the need exists for transfer-resistant, long-wear, comfortable and breathable cosmetic films which last until the consumer wants to remove them by washing or using remover compositions.

The present invention fulfills such a need and represents a significant advance in the cosmetic arts. None of the existing art provides the advantages and benefits of the present invention.

SUMMARY OF THE INVENTION

It is an object of the present invention to provide a cosmetic composition that undergoes in-situ curing on skin to provide a nanocomposite film.

It is another object of the present invention to provide a cosmetic composition providing a long-lasting, transfer-resistant, breathable and comfortable nanocomposite film.

It is another object of the invention to provide color cosmetic compositions, specifically lipsticks, that are long-lasting, transfer-resistant, comfortable and breathable.

It is yet a further object to provide a two-part system containing, a first part composition directed to a functionalized polymer and cross-linking agent (catalyst) and, a second part composition directed to POSS materials dissolved/dispersed in a cosmetic matrix, where the first and second parts are prevented from coming into intimate contact, together with the catalyst, prior to application on the skin.

In another aspect of the invention, the composition is a one part system or unfunctionalized polymer with Si—H or Si—OCH$_3$ functionalized POSS mixed with a cross-linking agent which is moisture-activated via application to pre-moistened keratinous material or applied concurrently with moisture and cures in-situ thereupon.

It is a further object of the present invention to provide a POSS based in-situ cross-linking composition having anti-tack or anti-block properties to reduce tackiness of cosmetic compositions.

Further according to this and other objects and advantages of the present invention are provided methods for applying (making up) and caring for mammalian keratinous material providing a long-lasting, transfer-resistant, breathable, and comfortable nanocomposite film comprising the steps of applying to mammalian keratinous material: a first part composition directed to a functionalized polymer and cross-linking agent and a second part composition directed to POSS materials dissolved in a cosmetic matrix, wherein said second part composition is topically applied after said first part composition.

It is also an object of the present invention to provide methods for making up and caring for mammalian keratinous material providing a long-lasting, transfer-resistant, breathable, and comfortable nanocomposite film comprising the steps of applying to mammalian keratinous material: a one-part composition containing functionalized or unfunctionalized polymer with Si—H or Si—OCH$_3$ functionalized POSS mixed with a cross-linking agent, which is moisture activated via application to pre-moistened or applied concurrently with moisture and cures in situ thereupon.

In another aspect of the invention, the present invention is applicable to the skin in any cosmetically acceptable vehicle. In various exemplary embodiments, the composition is a film.

The present invention is also directed to cosmetic kits for application of a cosmetic film composition comprising a first part composition containing a functionalized polymer and a cross-linking agent; and a second part composition comprising graftable POSS particles, wherein said second part composition is topically applied after said first part composition and methods of using the kit to effectively apply a film to mammalian keratinous material, especially the skin, face or lips.

The present invention also comprises a system for improving the transfer-resistance, sustainability and comfort of a cosmetic film wherein said system comprises cosmetic compositions comprising: a) a first part composition containing a functionalized polymer and a cross-linking agent; b) a second part composition comprising graftable POSS particles; and c) instructions indicating that the composition of b) should be applied after the composition of a).

These novel features of the present invention will become apparent to those skilled in the art from the following detailed description, which is simply, by way of illustration, various modes contemplated for carrying out the invention. As will be realized, the invention is capable of additional, different obvious aspects, all without departing from the invention. Accordingly, the figures and the specification are illustrative in nature and not restrictive.

DETAILED DESCRIPTION OF THE INVENTION

The inventors have discovered the use of graftable POSS in a cosmetic composition to form in-situ cross-linking chemistry. The present invention uses graftable POSS to tune the viscoelastic properties such as $T_g$, modulus (flexibility), mechanical properties, and optical properties for a graftable POSS nanocomposite obtained by in-situ cross-linking chemistry. Better spreadability over keratinous material can be achieved before cross-linking, so that the polymer chain has mobility to penetrate into pores and crevices on skin or hair surfaces. Once the second part composition containing graftable POSS particles is applied on top of the first composition, a network is formed by quick polymer-particle cross-linking, and mechanical interlocking inside of pores and crevices is also formed to provide better long-wear performance. Compared to simply mix POSS particles with polymer, the current in-situ cross-linking of a POSS nanocomposite improves long-wear properties or sustainability.

The composition according to the invention may be a makeup composition or a care composition for mammalian keratinous material, in particular, for the skin and the lips, and preferably, a makeup composition. The composition may also be a dermatological, personal care or pharmaceutical composition.

Advantageously, according to a first embodiment of the composition according to the invention, graftable POSS materials in a topical cosmetic composition undergo in-situ cross-linking on skin to provide a long-lasting, transfer-resistant, breathable and comfortable nanocomposite film. The cosmetic composition can be a one-part or two-part system. In one embodiment of the cosmetic composition the two-part system may be designed as follows: a first part composition (a) containing a functionalized polymer and cross-linking agent (catalyst) and a second part composition (b) containing POSS materials dissolved/dispersed in a cosmetic matrix. On mixing the two parts on skin, rapid curing leads to the formation of a highly elastic, flexible nanocomposite film with excellent adhesion (long-wear and smudge-resistant properties) and comfort.

Advantageously, according to a second embodiment of the composition according to the invention, the composition can be one-part system based on moisture-activated platinum-cured in-situ cross-linking. This is based on the chemistry of conversion of Si—H to Si—OH (in presence of platinum catalyst) followed by condensation to form a —Si—O—Si— network structure.

In this approach, an anhydrous cosmetic composition comprising functionalized or unfunctionalized polymer with Si—H functionalized POSS mixed with catalyst, or catalyst and pigment, can be packed in a package with moisture barrier. Application of this composition on pre-wet (saliva) lips would bring about in-situ cross-linking to form a non-tacky, long-wear film on the lips. The one-part composition represents an advantage to those for whom the need to apply two compositions to make-up the face or lips is unacceptable.

By the terms "cosmetic matrix" or "cosmetically acceptable medium" is meant substances permissible as ingredients in a cosmetic preparation that are compatible with mammalian keratinous material. The cosmetic matrix can be compounded with other essential ingredients.

As used herein, the term "keratinous material", used interchangeably with "keratinous tissue" refers to keratin-containing layers disposed as the outermost protective covering of mammals which includes, but is not limited to, skin, lips, hair (including eyebrows and eyelashes), and nails (toenails, fingernails, cuticles, hooves, etc.) of mammalians, preferably humans. However, as used herein, the term also includes the teeth and mucous membranes of the mouth.

Figure 1:
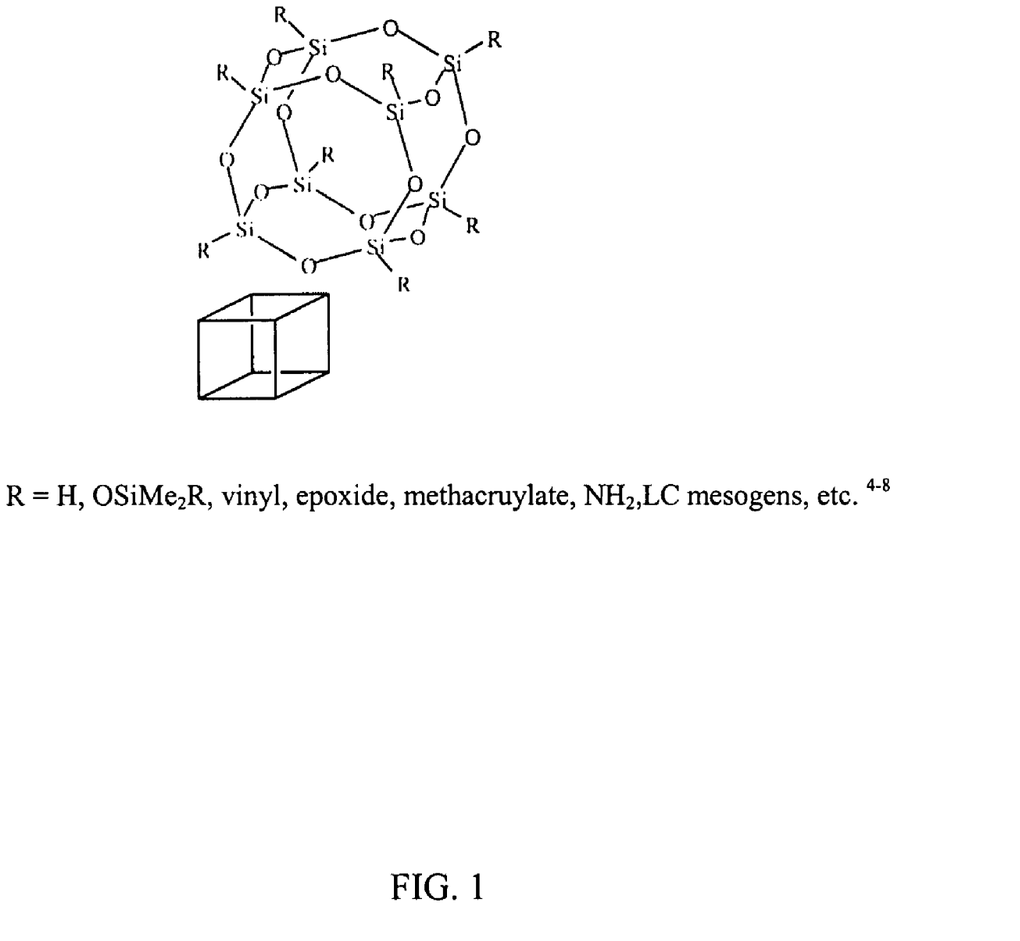
FIG. 1 is a representative sketch of POSS having molecular-level functional ingredients.

POSS are nano-sized inorganic materials with a silica core and reactive functional groups on the surface and represented by the general formula of $RSiO_{1.5}$. Graftable POSS, as used herein, refers to a mixture of Polyhedral Oligomeric Silsequioxane(s). Referring to FIG. 1, typical POSS materials have a cubic or three-dimensional cage-like structure with between six and eight silicon atoms attached to the cage of the cube and organic groups attached to each of the corners of the cube. Cubic silsesquioxanes, such as octa(dimethylsiloxy) silsequioxane ($R_8Si_8O_{12}$), consist of a rigid, crystalline silica-like core perfectly defined spatially (0.5-0.7 nm) which can be linked covalently to eight R groups. A description of possible cages is discussed in U.S. Pat. No. 5,942,638 and published articles, such as Silsequioxane-Siloxane Copolymers from Polyhedral Silsesquioxanes, *Macromolecules*, 1993, 26, p 2141-2142. Each of the cages can be further modified by attaching reactive moieties to the cage atoms. The core accounts for approximately 5% of the total volume and the highly enhanced surface effects. By designing the functionality of the R group, it is possible to create octa-functional macromonomers that will self-polymerize or copolymerize with other functionalized cubes to provide nanocomposites whose length scales and interfacial interactions are exactly defined. The structure of the organic phase between the rigid, hard particles can be varied systematically; the potential exists to carefully tune mechanical, optical properties to establish structure-property relationships.

Examples of suitable POSS compounds include, but are not limited to, dodecaphenyl, octaisobutyl and octamethyl POSS. POSS hybrid chemical compounds have molecular-level functional ingredients and are commercially available from Hybrid Plastics (Fountain Valley, Calif.) (www.hybridplastics.com).

More specifically, the POSS compounds include, but are not limited to, the following: 1-[3-(allylbisphenol A)propyldimethylsiloxy]-3,5,7,9,11,13,15 heptacyclopentylpentacyclo-[9.5.1.13,9.15,15.17,13]octasiloxane; 1-[3-(allylbiphenol)propyldimethylsiloxy]3,5,7,9,11,13,15 heptacyclopentylpentacyclo-[9.5.1.13,9.15,15.17,13]octasiloxane; 1-[3-(1,3-propanediol-2-ethyl-2-methyloxy)propyldimethylsiloxy]-3,5,7,9,11,13,15-heptacyclopentylpentacyclo-[9.5.1.13,9.15,15.17,13]octasiloxane; 1-[(2-methyl,2-hydroxy)butyldimethylsiloxy]-3,5,7,9,11,13,15-heptacyclopentylpentacyclo -[9.5.1.13,9.15,15.17,13]octasiloxane; 1-[3-(ethoxydimethylsilyl)propyl]3,5,7,9,11,13,15-heptacyclopentylpentacyclo[9.5.1.13,9.15,15.17,13]octasiloxane; 1-[2-(diethoxymethylsilyl)propyl]-5,7,9,11,13,15-heptacyclopentylpentacyclo [9.5.1.13,9.15,15.17,13]octasiloxane; 1-[3-(triethoxysilyl)propyl]3,5,7,9,11,13,15-heptacyclopentylpentacyclo[9.5.1.13,9.15,15.17,13]octasiloxane; 1-[2-(ethoxydimethylsilyl)ethyl]3,5,7,9,11,13,15-heptacyclopentylpentacyclo -[9.5.1.13,9.15,15.17,13]octasiloxane; 1-[2-(diethoxymethylsilyl)propyl]3,5,7,9,11,13,15-heptacyclopentylpentacyclo[9.5.1.13,9.15,15.17,13]octasiloxane; 1-[2-(triethoxysilyl)propyl]3,5,7,9,11,13,15-heptacyclopentylpentacyclo [9.5.1.13,9.15,15.17,13]octasiloxane; POSS-BisPhenol A-urethanes; POSS-DiMethylol-urethanes; 1-chloro-3,5,7,9,11,13,15-heptacyclopentylpentacyclo[9.5.1.13,9.15,15.17,13]octasiloxane; 1-[2-(chlorodimethylsilyl)ethyl]3,5,7,9,11,13,15heptacyclopentylpentacyclo[9.5.1.13,9.15,15.17,13]octasiloxane; 1-[2-(dichloromethylsilyl)ethyl]-3,5,7,9,11,13,15 heptacyclopentylpentacyclo[9.5.1.13,9.15,15.17,13]octasiloxane; 1-[2-(trichlorosilyl)ethyl]-3,5,7,9,11,13,15-heptacyclopentylpentacyclo[9.5.1.13,9.15,15.17,13]octasiloxane; 1-[3-(chlorodimethylsilyl)propyl]-3,5,7,9,11,13,15-heptacyclopentylpentacyclo -[9.5.1.13,9.15,15.17,13]octasiloxane; 1-[3-(dichloromethylsilyl)propyl]-3,5,7,9,11,13,15-heptacyclopentylpentacyclo[9.5.1.13,9.15,15.17,13]octasiloxane; 1-[3-(trichlorosilyl)propyl]-3,5,7,9,11,13,15-heptacyclopentylpentacyclo[9.5.1.13,9.15,15.17,13]octasiloxane; 1,3,5,7,9,11,13,15-[2-(chlorodimethylsilyl)ethyl]pentacyclo[9.5.1.13,9.15,15.17,13]octasiloxane; 1,3,5,7,9,11,13,15-[2-(chlorodimethylsilyl)ethyl]pentacyclo[9.5.1.13,9.15,15.17,13]octasiloxane; 1,3,5,7,9,11,13,15-[2-(dichlorodimethylsilyl)ethyl]pentacyclo [9.5.1.13,9.15,15.17,13]octasiloxane; 1-[(2-epoxy)propyl]-3,5,7,9,11,13,15-heptacyclopentylpentacyclo[9.5.1.13,9.15,15.17,13]octasiloxane; 1-[2-(cyclohexyl-3-epoxy)ethyl]-3,5,7,9,11,13,15-heptacyclopentylpentacyclo [9.5.1.13,9.15,15.17,13]octasiloxane; POSS-diepoxide resins; 1,3,5,7,9-octavinyl-11,13,15-epoxyethylpentacyclo[9.5.1.1.3,9.1.15,15.1.17,13]octasiloxane; endo-3,7,14-tris[1-(3-dimethylsiloxy)propyloxy-2,3-epoxypropyl]-1,3,5,7,9,11,14,-heptacyclopentyltricyclo[7.3.3.1,5,11]heptasiloxane; 1-(methylpropionato)-3,5,7,9,11,13,15-heptacyclopentylpentacyclo[9.-5.1.1.3,9.15,15.17,13]octasiloxane; 1 (ethylundecanoato) -3,5,7,9,11,13,15-heptacyclopentylpentacyclo[9.-5.1.1.3,9.15,15.17,13]octasiloxane; 1-[(3-chloro)propyl]-3,5,7,9,11,13,15-heptacyclopentylpentacyclo[9.5.1.13,9.15,15.17,13]octasiloxane; 1-[4-chlorophenyl]-3,5,7,9,11,13,15-heptacyclopentylpentacyclo[9.5.-1.13,9.15,15.17,13]octasiloxane; 1-[chlorobenzyl]-3,5,7,9,11,13,15-heptacyclopentylpentacyclo[9.5.1.13,9.15,15.17,13]octasiloxane; 1-[2-(chlorobenzyl)ethyl]-3,5,7,9,11,13,15-heptacyclopentylpenta-cyclo [9.5.1.13,9.15,15.17,13]octasiloxane; 1-[3-(methacryl)propyl]-3,5,7,9,11,13,15-heptacyclopentacyclo[9.5.1.13,9.15,15.17,13]octasiloxane; 1-[3-(methacryl)propyldimethylsiloxy]-3,5,7,9,11,13,15-heptacyclopentylpentacyclo -[9.5.1.13,9.15,15.17,13]-octasiloxane; 1-(3,3,3-trifluoropropyldimethylsiloxy) -1,3,5,9,11,13,15-heptacyclopentyl-7-[3-(methacryl)propyl]-7-methyltetracyclo[9.5.1.15,11.19,15]octasiloxane; 1-(tridecafluoro-1,1,2,2-tetrahydrooctyldimethylsiloxy)-1,3,5,9,11,13,15-heptacyclopentyl-7-[3-(methacryl)propyl]-7-methyltetracyclo[9.5.1.15,11.19,15]octasiloxane; 1-(trimethylsiloxy)-1,3,5,9,11,13,15-heptacyclopentyl-7-[3-(methacryl)propyl]-7-ethyltetracyclo[9.5.1.15,11.19,15]octasiloxane; 1,3,5,7,9-pentavinyl-11,13,15-[1-hydroxy-2-(methacryl)ethyl]pentacyclo[9.5.1.13,9.15,15.17,13]octasiloxane; 1,3,5,7,9,11-hexacyclohexyltetracyclo[5.5.1.13,11.15,9]hexasiloxane; 1,3,5,7,9,11,13,15-octacyclohexylpentacyclo[9.5.1.13,9.15,15.17,13]octasiloxane; 1,3,5,7,9,11,13,15-octacyclopentylpentacyclo[9.5.1.13,9.15,15.17,13]octasiloxane; 1,3,5,7,9,11,13,15-octaphenylpentacyclo[9.5.1.13,9.15,15.17,13]octasiloxane; 1,3,5,7,9,11,13,15-octamethylpentacyclo[9.5.1.13,9.15,15.17,13]octasiloxane; 1,3,5,7,9,11,13,15-octakis(dimethylsilyloxy)pentacyclo[9.5.1.13,9,1-.5,15.17,13]octasiloxane; POSS-modified Nylon 6; 1-[(3-cyano)propyl-3,5,7,9,11,13,15-heptacyclopentylpentacyclo[9.5-.1.1. sup.3,9.15,15.17,13]octasiloxane; 1-[2-(Norbornen-2-yl)ethyl]-3,5,7,9,11,13,15-heptacyclopentylpentacyclo[9.5.1.13,9.15,15.17,13]octasiloxane; 1-[2-(Norbornen-2-yl) ethyldimethylsiloxy]-3,5,7,9,11,13,15heptacyclopentylpentacyclo[9.5.1.13,9.15,15.17,13]-octasiloxane; poly(ethylnorbornenylPOSS-co-norbornene); 1,1,3,3-(norbornenyldimethylsiloxy)-1,3,-dicyclohexyldisiloxane; 1-[3-(allylbisphenol A)propyldimethylsiloxy]-3,5,7,9,11,13,15 heptacyclopentylpentacyclo -[9.5.1.13,9.15,15.17,13]octasiloxane; 1-[3-(allylbiphenol)propyldimethylsiloxy]-3,5,7,9,11,13,15 heptacyclopentylpentacyclo-[9.5.1.13,9.15,15.17,13]octasiloxane; 1,3,5,7,9,11,13,15-octavinylpentacyclo[9.5.1.13,9.15,15.17,13]octasiloxane; 1-vinyl-3,5,7,9,11,13,15-heptacyclopentylpentacyclo[9.5.1.13,9.15,15.17,13]octasiloxane; 1-allyl -3,5,7,9,11,13,15-heptacyclopentylpentacyclo[9.5.1.13,9.15,15.17,13]octasiloxane; 1-[2-(cyclohexen-3-yl)ethyl]-3,5,7,9,11,13,15-heptacyclopentylpentacyclo[9.5.1.13,9.15,15.17,13]octasiloxane; poly (dimethyl-co-methylvinyl-co-methylethylsiloxyPOSS)siloxane; POSS-diepoxide resins; POSS-Bis Phenol A-urethanes; 1-[2(diphenylphosphino)ethyl]3,5,7,9,11,13,15-heptacyclopentylpentacyclo [9.5.1.13,9.15,15.17,13]octasiloxane; 1-[2(diphenylphosphino)propyl]3,5,7,9,11,13,15-heptacyclopentylpenta-cyclo [9.5.1.13,9.15,15.17,13]octasiloxane; 1-hydrido-3,5,7,9,11,13,15-heptacyclopentylpentacyclo[9.5.1.13,9.15,15.17,13]octasiloxane; 1-[hydridodimethylsiloxy]-3,5,7,9,11,13,15-heptacyclopentylpentacyclo[9.5.1.13,9.15,15.17,13]octasiloxane; endo-3,7,14-tri(dimethylsilylhydrido)-1,3,5,7,9,11,14-heptacyopentyl-tricyclo[7.3.3.15,15,11]heptasiloxane; 1,1,3,3-(hydridodimethylsiloxy)-1,3-dicyclohexyldisiloxane; poly(dimethyl-co-methylhydrido-co-methylpropyl POSS)siloxaneendo-3,7,14-trihydroxy-1,3,5,7,9,11,14-heptacyclopentyltricyclo[7.3.3.15,11]heptasiloxane; endo-3,7,14-trihydroxy-1,3,5,7,9,11,14-heptacyclohexyltricyclo[7.3.-3.15,11]heptasiloxane; 1-hydroxy-3,5,7,9,11,13,15-heptacyclopentylpentacyclo[9.5.1.13,9.15,15.17,13]octasiloxane; 1,1,3,3-(tetrahydroxy)-1,3-dicyclohexyldisiloxane; 1,3,5,7-(tetrahydroxy)-1,3,5,7-(tetraphenyl)cyclotetrasiloxane; endo -7,14-dihydroxy-3-(3,3,3-trifluoropropyldimethylsiloxy)-1,3,5,9,11,13,15-heptacyclopentyltricyclo[7.3.3.15,11]octasiloxane; 1,3,5,7-(tetrahydroxy)-1,3,5,7, -(tetraphenyl)

cyclotetrasiloxane; endo-7,14,-dihydroxy-3-(3,3,3-trifluoropropyldimethylsiloxy)-1,3,5,9,11,13,15-eptacyclopentyltricyclo[7.3.3.1$^{5,11}$]octasiloxane; 1-[2-(styryl)ethyldimethylsiloxy]-3,5,7,9,11,13,15-heptacyclopentyl-pentacyclo [9.5.1.13,9.15,15.17,13]-octasiloxane; 1-[(4-vinyl)phenyl]-3,5,7,9,11,13,15-heptacyclopentylpentacyclo[9.5.1.13,9.15,15.17,13] octasiloxane; 1-[2-(styryl)ethyl]-3,5,7,9,11,13,15-heptacyclopentylpentacyclo[9.5.1.13,9.15,15.17,13]-octasiloxane; R=cyclopentyl, TMP DiolCyclopentyl-POSS; R=i-butyl, Trans-CyclohexaneDiolisobutyl-POSS; R=i-butyl, 1,2-PropaneDiolisobutyl-POSS; R=i-butyl, Aminopropylisobutyl-POSS; R=i-octyl, Aminopropylisobutyl-POSS; R=i-butyl, Aminoethylaminopropylisobutyl-POSS; R=Cyclopentyl, IsocyanatopropyldimethylsilylCyclopentyl-POSS; R=i-butyl, MethacrylisobutylTitanium-POSS; OctaAmmonium-POSS; OctaAmmonium-POSS; Poly (styryl POSS-co-styrene); poly(vinylsilsesquioxane); and structures having 10 and 12 silicon atoms in the cage.

The POSS of the present invention may be prepared by hydrolytic condensation reactions of trifunctional organosilicone monomers, e.g. RSi(OMe). Methods of preparing POSS are described in U.S. Pat. No. 6,372,843 which is incorporated by reference in its entirety herein.

Figure 2:
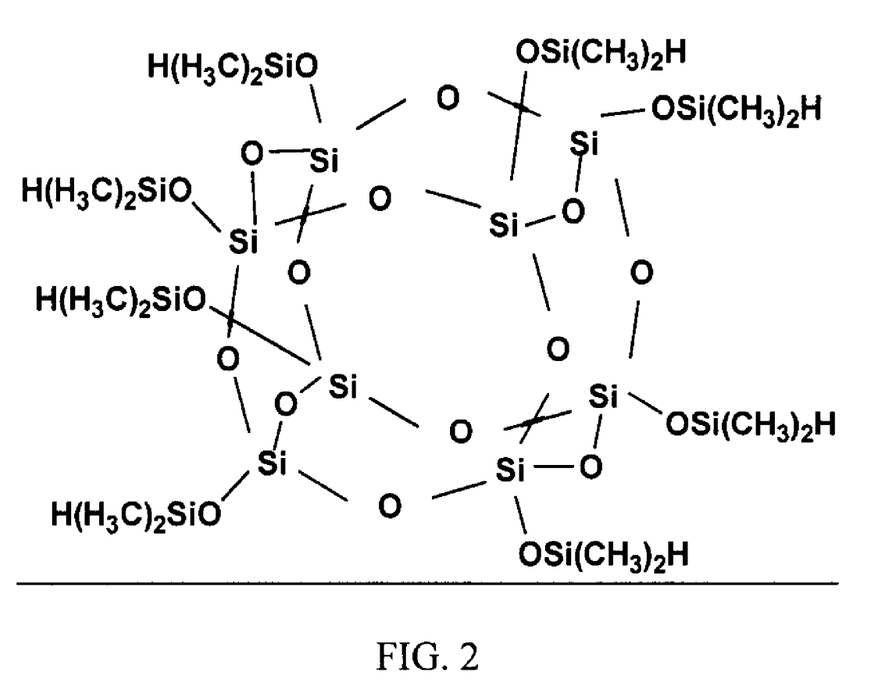
FIG. 2 is a representative sketch of POSS with Si—H groups on the cage.

The nanocomposite cosmetic composition on mammalian keratinous material can be obtained by selecting a functionalized polymer and POSS materials along with an appropriate catalyst. The POSS and polymer molecules are functionalized with at least one group or a plurality of groups. Examples of functional groups on the polymer and POSS materials include, but are not limited to, functional silicones—for example, hydroxy, urethane, acrylate, vinyl, Si—H, amides, MQ or T groups, functional acrylates, functional polyamides, PVK, PVA, PS, PEG, PPG, polysaccharides or modified starch, functional block copolymers, functional polyesters and polyesters, fluorinated polymers and wax to bring about the cross-linking reaction between the polymer chains and POSS materials to provide desired properties. The structure of POSS with Si—H groups is presented in FIG. 2. The inorganic Si—O core of the silsequioxane cages are compatible with organic matrixes, yielding a nanocomposite with molecular-level dispersion. Properties of POSS based nanocomposite film such as elasticity, flexibility, adhesion, gloss, shrinkage, (permeability) breathability can be tuned by controlling the degree of cross-linking either by changing the number of reactive sites on POSS or by changing weight fractions. For example, the self-assembly behavior of POSS with polymers can be varied by functionalizing only one of the cube corners.

Figure 3:
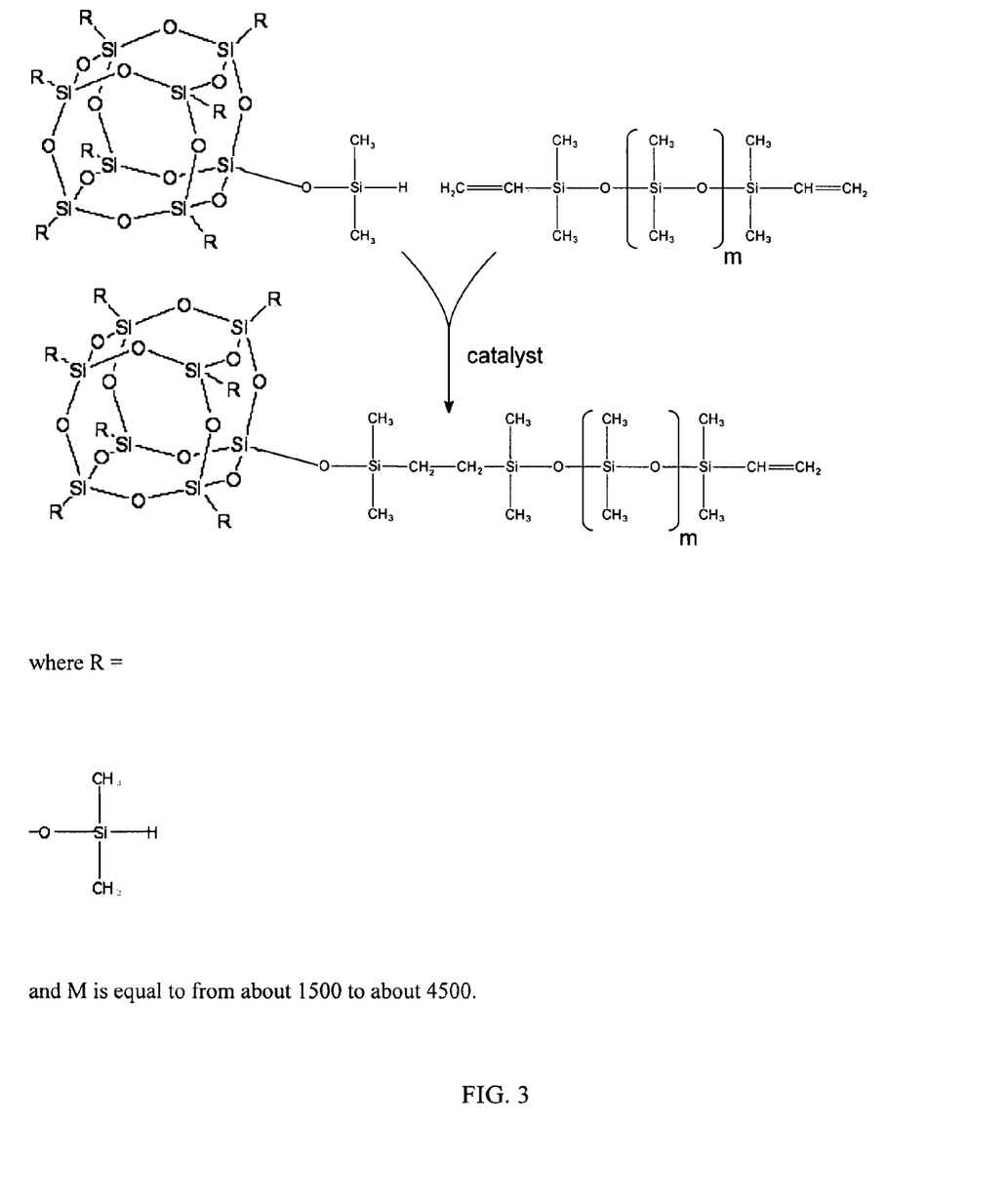
FIG. 3 represents a schematic of the hydrosilylation reaction.

Referring to FIG. 3, crosslinked POSS is prepared by the hydrosilylation addition reaction between POSS and the functionalized polymer, divinyl-terminated polydimethylsiloxane (PDMS). The reaction is performed with or without the presence of a catalyst which is a platinum compound. The cross-linking catalyst functions to induce in-situ cross-linking of the POSS through the addition reaction of Si—H to the terminal groups or side chains.

Figure 4:
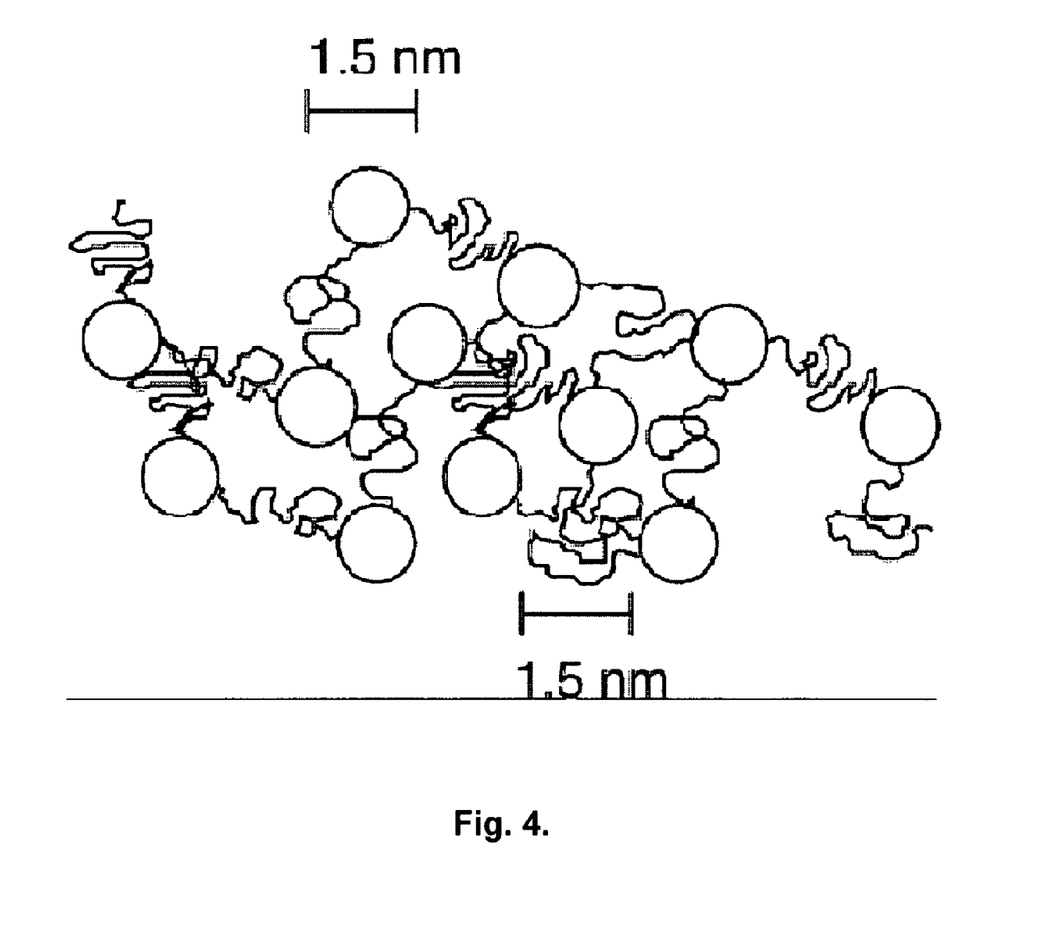
FIG. 4 represents a schematic of POSS-based composite film.

FIG. 4 shows a schematic of POSS based nanocomposite cosmetic film. The size of the POSS cage is comparable to the dimensions of the polymer, enabling POSS to control the motions of the chains at the molecular level resulting in true molecular level (nanoscopic) distribution of POSS in nanocomposites. Thus, such nanoreinforced cosmetic composition can provide significant enhancement in adhesive and mechanical properties (flexibility with elastic strength) while improving or retaining the material's other physical properties (optical clarity, mechanical, feel, etc.) as well as its processability (without unusual increase in viscosity with loading). That is, even at very low particle content the nanocomposite film of the present invention exhibits optimal properties. In addition to the above benefits, improved moisture permeability (breathable film) to provide comfort is also achieved. The deposit obtained on the skin or lips does not cause the user any sensation of drying out or tautness. Advantageously, the deposit is thus comfortable.

The present invention is directed to POSS materials with graftable sites along with polymers with complimentary functional groups in the presence of suitable catalyst to bring about in-situ cross-linking on skin. The nanocomposite cosmetic film formed on skin by in-situ cross-linking is expected to provide long-lasting, transfer-resistant, elastic, breathable film with comfort. Increase in gloss is achieved due to increase in refractive index of the nanocomposite films. Thus, one can achieve mutually exclusive properties such as long-wear (adhesion) with comfort with a high gloss product. POSS materials used for in-situ crosslinked nanocomposite composition provide molecular level control to tune the properties of the skin. One can obtain truly molecular level interaction with tunable interfacial properties. One can change physical properties such as increased glass transition temperature, low density, increased permeability, lowered thermal conductivity, increased mechanical properties (modulus of elasticity), increased creep resistance (creep is time-dependent deformation at absolute temperatures greater than one half the absolute melting), reduced viscosity, ease of application and increased refractive index.

The present invention is a polymer-nanoparticle in-situ cross-linking, which results in an organic-inorganic hybrid nanocomposite. Furthermore, the POSS particle has high surface area and multiple graftable sites which allow faster cross-linking even at very low loadings to provide a long-lasting cosmetic composition on skin or lips. The film generated by less than 1% POSS particles is comparable to the one generated by 30% hydrosilane polymer with superior wear properties such as long-wear, gloss, elasticity, comfort, etc.

POSS based in-situ cross-linking composition can also be used as an anti-tack or anti-block agent to reduce tackiness for some cosmetic composition by surface cross-linking. The film of the present invention has a maximum tensile strength of less than or equal to about 10 MPa, and preferably less than about 5 MPa. Additionally, the film has little to no surface stickiness, i.e., after contact between the finger and the surface of the film, no impression of stickiness of the surface is experienced when contact is broken therewith by removing the finger.

It is preferred that the average diameter of cross-linked POSS in the film of the present invention be within a range of 0.1 to 100 nm, preferably within a range of 0.7 to 50 mm.

The amount of POSS depends on the desired final use, the role of POSS in the product, and the amount of other components used in the composition, and other factors well known to formulators. It can range, for example, from about 0.001 to about 50% weight, preferably from about 0.05 to about 20% weight, and more preferably from about 0.5 to about 15% weight based on the total weight of the composition.

The polymer of the present invention provides many materials choices in terms of commercial availability of materials. For example, one can choose PDMS blend along with Si—H functionalized POSS in presence of Pt catalyst. POSS will self-crosslink in a non-volatile polydimethylsiloxane (PDMS) matrix to form an interpenetrating network. Among the polyalkylsiloxanes that may be used according to the present disclosure, non-limiting examples include polydimethylsiloxanes, (polydimethylsiloxane)/(methylvinylsiloxane) copolymers, poly(dimethylsiloxane)(diphenyl)siloxanes and poly(dimethylsiloxane)(diphenyl)(methylvinylsiloxane) copolymers, and mixtures thereof. Suitable polydimethylsiloxanes have the formula X[—Si(CH$_3$)$_2$O—]$_N$X where N>1000. Other polyorganosiloxane polymers may also be used. Non-limiting examples include siloxy-silicates, polysilsesquioxanes and polymethylsesquioxanes, polydimethylsiloxanes comprising alkyl, alkoxy or phenyl groups, which are pendent or at the end of a silicone chain, these groups comprising from 2 to 24 carbon atoms; phenyl silicones, for example, phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates.

Preferred are high viscosity polydimethylsiloxane polymers which yield linear polymers with average kinematic viscosities ranging from 10,000-3,000,000 cSt, preferably 50,000 to 2,000,000 cSt. The viscosity herein can be suitably measured by Brookfield LV at 20 rpm at 25° C.

In at least one embodiment, the polymer is a polydimethylsiloxane such as Dow Corning 200 Fluid (100,000 cSt). Other examples include those from the 200 series (Dow Corning) 224, 245, 344, 246, and 200 fluids, the Vicasil® series (General Electric), and other materials and mixtures commercially available from Gelest and Hybrid Plastics.

The functionalized polymer may be present in amounts ranging from about 0.05-50%, preferably about 0.5-30%, and most preferably about 5-20%.

As used herein, the term "film-forming polymer" refers to a polymer capable of forming, by itself alone or in the presence of an additional agent which is able to form a film, a continuous film that adheres to a support, especially to mammalian keratin tissue.

The term "functionalized" or "functional polymer" as used herein refers to a polymer that exhibits specific chemical reactivity or binds selectively to particular species. The POSS nano-particles may be functionalized in any method known to those skilled in the art.

The term "cross-linking", as used herein, refers to a reaction involving pairs of polymer chains that result in the formation of small regions in a polymer from which at least four chains emanate.

The phrase "interpenetrating network" as used herein refers to the physical anchor of a long-chain polymer in a supporting polymer/particle network that is normally non-swellable in water. One end of the polymer becomes entwined or chemically bound with the supporting polymer/particle network.

The phrase "non-transferable" or "transfer-resistant" refers to forming a deposit that does not become at least partially deposited onto the supports with which it comes into contact (e.g. glass, coffee cups, kiss proof, clothing, cigarettes).

The term "breathable" as used herein refers to permeability of small molecules such as oxygen, carbon dioxide, water through the mammalian keratinous tissue. It is understood that the film is both permeable and waterproof.

The hydrosylilation reaction catalyst contained in the cross-linkable silicone composition of the present invention is a catalyst for acceleration of cross-linking of the composition. Preferably, it should be a platinum catalyst such as chloroplatinic acid, an alcoholic solution of chloroplatinic acid, an olefin complex of platinum, an alkenylsiloxane complex of platinum, platinum black, or silica on a platinum carrier. Other specific examples of suitable platinum catalysts include, but are not limited to, platinum metal; solid platinum supported on a carrier such as alumina, silica or carbon black; chloroplatinic acid; a complex of chloroplatinic acid with an alcohol, an aldehyde or a ketone; a platinum-olefin complex (for example, Pt(CH$_2$=CH$_2$)$_2$ (PPh$_3$)$_2$ Pt(CH$_2$=CH$_2$)$_2$ Cl$_2$); a platinum-vinylsiloxane complex (for example, Pt$_n$(ViMe$_2$SiOSiMe$_2$Vi)$_m$, Pt[(MeViSiO)$_4$]$_m$); a platinum-phosphine complex (for example, Pt(PPh$_3$)$_4$, Pt(PBu$_3$)$_4$); a platinum-phosphite complex (for example, Pt[P(OPh)$_3$]$_4$, Pt[P(OBu)$_3$]$_4$) (wherein Me is a methyl group, Bu is a butyl group, Vi is a vinyl group, Ph is a phenyl group, and n and m are an integer); dicarbonyldichloroplatinum; a platinum-hydrocarbon complex described in U.S. Pat. Nos. 3,159,601 and 3,159,662 to Ashby, herein incorporated by reference in their entirety; and a platinum alcoholate catalyst described in U.S. Pat. No. 3,220,972 to Lamoreaux. In addition, a chloroplatinum-olefin complex described in U.S. Pat. No. 3,516,946 to Modic is also useful in the present invention; each of which is incorporated by reference in its entirety.

Other hydrosilylation catalysts are described in, for example, U.S. Pat. Nos. 6,307,082, 5,789,334, 4,681,963, 3,715,334, 3,775,452, 3,814,730, 3,159,601, 3,220,972, 3,576,027, and 3,159,662, the disclosures of which are hereby incorporated by reference in their entirety. More specifically, examples of catalysts other than platinum compounds are Group VIII metals such as rhodium or palladium compounds similar thereto such as RhCl(PPh$_3$)$_3$, RhCl$_3$, Rh/Al$_2$O$_3$, RuCl$_3$, IrCl$_3$, FeCl$_3$, AlCl$_3$, PdCl$_2$.2H$_2$O, NiCl$_2$ and TiCl$_4$ (wherein Ph is a phenyl group). One catalyst or combinations of at least two catalysts may be used. In view of catalytic activity, chloroplatinic acid, the platinum-olefin complex, the platinum-vinylsiloxane complex and the like are preferable. Additionally, mixtures may be used such as those sold by Dow Corning under the references Dow Corning 8-8024 Curing Agent and Dow Corning 200 Fluid, 0.65 cSt which is 0.65 cSt disiloxane.

Suitable commercially available hydrosilylation (addition) cross-linking compositions which may be readily formulated into such one or two-part systems include without limitation Dow Corning 8-8024 Base and Dow Corning 8-8024 Curing Agent, Dow Corning 7-9800 Part A&B Soft Skin Adhesive™, and Dow Corning 7-6800 Part A&B Silky Touch™, Dow Corning's Silastic® Liquid Silicone Rubber (LSR), Dow Corning C6 LSR serial, Silastic® Q7 serial, Silastic® 590 LSR Part A&B, Silastic® 591 LSR Part A&B, Silastic® LSR 9150200P, Silastic® LSR 9451-1000P, and Silastic® 5-8601 LSR Worosilicone materials. Similar LSR products are available from General Electric Advanced Materials under the names Siloprene® LSR, LIMO LSR, LSR Topcoat, and Addisil®. Two-part Room Temperature Vulcanizing (RTV) Rubbers from GE and Dow Corning under the names IRTV615 and RTV627 provide additional examples of commercially available hydrosilylation (addition) cross-linking systems.

A cross-linkable silicone composition that contains the hydrosylilation catalyst in water can be prepared by dispersing in water the cross-linkable silicone composition which has been premixed with the hydrosylilation catalyst, or the catalyst can be added to water after dispersing it in the catalyst-free cross-linkable silicone composition. It is preferred to use an aqueous dispersion containing the hydrosylilation catalyst with an average particle diameter not exceeding 1 μm. It is also preferred that the hydrosylilation catalyst be used in the cross-linkable composition in an amount sufficient for accelerating the cross-linking of the cross-linkable composition. For example, when a platinum-system catalyst is used as a hydrosylilation catalyst, it should be used in an amount of about $1 \times 10^{-7}$ to about $1 \times 10^{-3}$ parts by weight of platinum metal per 100 parts by weight of the POSS. However, it is understood that the amount of catalyst is not limited.

Preferably, an inert carrier is also present to solubilize the POSS and provide for efficient application. There is essentially no constraint on the selection of carrier. However, the carrier should ideally be anhydrous, unreactive in the presence of the POSS, and compatible with a cosmetic or personal care product. Suitable carriers include, for example, hydrocarbon oils, including without limitation $C_8$-$C_{20}$ hydrocarbons such as isododecane, and silicone oils including without limitation hexamethyldisiloxane (HMDS), polydimethylsiloxane (dimethicone) polymers, and cyclodimethicones. Suitable non-volatile dimethicone polymers are available from Dow Corning under the name Dow Corning 200® Fluid and have viscosities ranging from 5 to 600,000 centistokes. Others may be used such as the Viscasil series of polyalkylsiloxanes (General Electric Company) and the Dow Corning 200 series (Dow Corning Corp.). Suitable polyalkylarylsiloxanes include polymethylphenyl siloxanes having viscosities of from about 15 to about 65 centistokes at 25° C. such as, for example, those available as SF 1075 methyl-phenyl fluid (General Electric Company) and 556 Cosmetic Grade Fluid (Dow Corning Corp.). Useful polyethersiloxane copolymers include, without limitation, a polyoxyalkylene ether copolymer having a viscosity of about 1200 to 1500 centistokes at 25° C., including for example, SF1066 organosilicone surfactant (General Electric Company).

The carrier will typically comprise from about 10% to about 90% by weight of the film-forming composition, and more typically between about 30% and about 80% by weight. In preferred embodiments, the carrier comprises between about 50% and about 70% by weight of the film-forming composition.

By means of a cross-linking reaction, the cross-linkable silicone composition can be converted to a rubber-like, gel-like or a similar elastomeric cross-linked film.

i. One-Part Systems

In a one-part system, the POSS, polymer and catalyst will necessarily be packaged together. Various methods for preventing the cross-linking reaction from occurring prior to application may be envisaged, all of which are contemplated to be within the scope of the invention. However, particular embodiments described below are considered to be currently preferred.

In one embodiment of the invention, the one-part system comprises a continuous phase of functionalized or unfunctionalized polymer with Si—H/Si—$OCH_3$ functionalized POSS mixed with catalyst and a disperse phase comprising a plurality of microcapsules dispersed in the continuous phase. Because it is necessary to prevent the three components (POSS, polymer, and catalyst) from coming into contact prior to use, either the POSS or the catalyst may be disposed within the plurality of microcapsules. Preferably, the catalyst is contained within the microcapsules. Only when the microcapsules are ruptured or otherwise degraded do the three components come into intimate contact and thus initiate the cross-linking reaction.

As is well known in the art, encapsulating materials can be selected which will release the catalyst upon exposure to moisture, pH change, temperature change, solubility change, or mechanical shear. Suitable encapsulating materials and methods of preparing encapsulated materials, such as spray drying, extrusion, coacervation, fluidized bed coating, liposome entrapment and others, are disclosed in, for example, U.S. Pub. No. 20050000531; Jens Uhlmann, Brigit Schleifenbaum, Heinz-Jurgen Bertram, "Flavor encapsulation technologies: an overview including recent developments" *Perfumer and Flavorist*, 27, 52-61, 2002; and "Selection of Coating and Microencapsulation Processes" by Robert E. Sparks and Irwin Jacobs in *Controlled-Release Delivery Systems for Pesticides*, Herbert B. Scher ed., Marcel Dekker, New York, N.Y., 1999, pp 3-29, the contents of which are hereby incorporated by reference in their entirety. Moisture sensitive microcapsules will suffer the disadvantage of requiring anhydrous conditions prior to use and are therefore less preferred than microcapsules which release their contents by other mechanisms when employed in re-usable formulations where ambient moisture may be introduced into the packaging during use.

It is also contemplated that one-part systems may be formulated where all three components are present in admixture along with a hydrosilylation inhibitor which prevents the cross-linking reaction from occurring prior to the occurrence of a triggering event such as evaporation or sublimation of the inhibitor, temperature increase, pH change, photo-activation and the like. Non-limiting examples of hydrosilylation inhibitors are described in U.S. Pat. Nos. 3,445,420, 4,256,870, 4,465,818, 4,562,096, and 5,629,387, the disclosures of which are hereby incorporated by reference in their entirety. It is well within the skill in the art to select a suitable hydrosilylation inhibitor.

The one-part systems may be packaged in any conventional manner, including bottles, tubes, tubs, and the like. When so packaged the composition may be applied to the biological surfaces with any type of applicator known in the art, including sprays, swabs, brushes, towelettes, and applicator tips integral with the package.

ii. Two-Part Systems

In another embodiment of the invention, the POSS and the catalyst are physically separated prior to use. The system may be in the form of a first component comprising the Si—H functionalized polymer and catalyst and a second component comprising the POSS dissolved/dispersed in a cosmetic matrix. Both the first and second components may further comprise a carrier material, as described above.

The first and second components may be packaged separately, for example in two containers, bottles, tubes, and the like, or may be packaged in one container having a physical partition which prevents the first and second components from coming into contact as described in, for example, U.S. Pub. No. 2004/0165935 A1 and U.S. Design Pat. D449,224, D326,606 and U.S. Pat. Nos. 6,789,971, 6,247,586, 5,318,203, 4,196,808 and 3,757,782 the contents of which are hereby incorporated by reference in their entirety.

In use, it is preferred to first apply the component comprising the functionalized polymer and catalyst to a surface as a base coat. Thereafter, the component comprising the POSS dispersed in a cosmetic matrix is applied as a top coat over the base coat. The base and top coats are applied onto the surface sequentially with a mixing ratio from about 1:1 to about 5:1. Alternatively, the first and second components may be mixed immediately prior to use and applied as one coating to the surface.

Alternatively, the first and second parts are separated by a dual component package, such as a dual cartridge with a mixer nozzle and applied as a single step. The skilled artisan will recognize that the foregoing embodiments are merely illustrative and all systems in which the three components are prevented from reacting prior to use are considered to be within the scope of the invention.

The first or second components may optionally comprise an agent for accelerating the hydrosilylation (addition) reaction. Such agents are well known in the art and disclosed in, for example, U.S. Pat. No. 6,303,728, the disclosure of which is hereby incorporated by reference in its entirety. There are no special limitations with regard to the amount of water used in the method. It is preferred, however, that water be used in an amount of about 5 to 99 wt. %, preferably about 10 to 80 wt. %, based on the total weight of the composition.

Optionally, either the first part of the composition or the second part may have one or more ingredients such as, but not limited to, a filler, film-forming polymers, pigments, nacres, waxes, oils, humectants, vitamins, fragrances, surfactants, stabilizers, preservatives, particulates, flavor oils, skin care ingredients such as sunscreen, emulsifiers and the like. Hypoallergenic compositions can be made into the present invention where said compositions do not contain fragrances, flavor oils, lanolin, sunscreens, particularly PABA, or other sensitizers and irritants. There are a great number of other ingredients approved for use in the cosmetic art that may be used in compositions of the present invention. Such ingredients are those approved for use in cosmetics and can be found listed in reference books such as the CTFA Cosmetic Ingredient Dictionary & Handbook, Tenth Edition, The Cosmetic, Toiletries, and Fragrance Association, Inc. 2004 which is hereby incorporated by reference. Said materials may be used so long as they satisfy the criteria of not significantly disrupting the film once applied.

A preservative may be added to either the first or second composition. Suitable preservative agents include the parabens or sodium benzoate and mixtures thereof. However, any preservative known to those skilled in the art may be used. The preservative concentration in the cosmetic composition based on the total weight of the composition is in the range of between about 0.5% and about 1% by weight, preferably between about 0.1% and about 0.3% by weight.

A pigment, dye, or nacres may be added to either the first or second part composition. The pigment is generally in an amount from about 0.1% by weight relative to the total weight of the composition, preferably from about 1% to about 30% by weight.

The term "filler" means any material selected from mineral or organic, laminar, spherical or oblong fillers, that are chemically inert in the first or second part composition.

A filler may be added either for adjusting its flowability or improving the mechanical strength of the obtained cross-linked silicone particles. Examples of suitable fillers are precipitated silica, fumed silica, baked silica, mica, talc, fumed titanium oxide, kaolin, or a similar reinforcing filler; crushed quartz, diatomaceous earth, aluminosilicic acid, ferrous oxide, zinc oxide, calcium oxide, polyamide powders, powders of tetrafluoroethylene polymers, starch, hollow polymer microspheres, acrylic polymers particles and mixtures thereof, or a similar non-reinforcing filler. The surfaces of these fillers can be treated with hexamethylsiloxane, trimethylchlorosilane, polydimethylsiloxane, polymethylhydridosiloxane, or similar organosilicone compounds.

The composition may comprise, in addition to the functional polymer described above according to the invention, at least one additional or auxiliary polymer such as a film-forming polymer. The auxiliary polymer may be a coalescer or a plasticizer known to those skilled in the art. A plasticizer is generally an organic compound that remains in the composition during the formation of the film. A coalescer is generally a volatile organic compound that evaporates off during the formation of the film.

The at least one additional film-forming polymers that may be used in the composition of the present invention include, but are not limited to, synthetic polymers, natural polymers and mixtures thereof. Film-forming polymers that may be mentioned in particular include acrylic polymers, polyurethanes, polyesters, polyamides, polyurea, and cellulose-based polymers, such as nitrocellulose. The at least one film forming polymer can be present in the composition according to the present invention in an amount ranging from about 0.1% to about 60% by weight, preferably from about 3% to about 30% relative to the total weight of the composition.

The terms "a" and "an", as used herein and in the appended claims, mean "one or more" unless otherwise indicated herein.

Except where specific examples of actual measured values are presented, numerical values referred to herein should be considered to be qualified by the word "about."

The cosmetic compositions may be in the form of cosmetically acceptable vehicles, such as, but not limited to, liquid (e.g. suspension or solution), gel, emulsion, emulsified gel, mousse, cream, ointment, lotion, spray, wipe, paste, serum, milk, foam, balm, aerosol, liposomes, solid (e.g. pressed powders), cake, mask, anhydrous oil and wax composition. For example, the composition may be sprayed from a can or canister. More specifically, the cosmetic may include facial skin care cosmetics such as a skin lotion, skin milk, skin cream, gel, skin softener, and make-ups such as foundation, foundation primer base, blush, lipstick, eyeshadow, eye liner, nail enamel, concealer, mascara, body make-up product, a sunscreen, or hair makeup product. The care composition may be a body and facial skin care product (lipstick), especially an anti-sun product or a skin coloring product such as a self-tanning product. The composition may also be a hair care product, especially for thickening, holding or shaping the hair or hairstyle.

The cosmetic composition is accordance with the invention may be in a variety of forms. Preferably, the composition is used in a lipstick. A glossy lip makeup is obtained which is comfortable, does not make the lips taut, and has good staying power, does not migrate or transfer, and is easy to remove.

Preferably, the composition is especially suitable where long-lasting cosmetic effects are desired such as sunscreens, insect repellants, lipstick, lip gloss, mascara, foundation, leave on conditioners for damaged hair, semi-permanent makeup products such as tattoos, dots or patches that adhere to the skin (such as beauty marks or glitters) as well as skin care products such as masks, and overnight treatments.

Additionally, the cosmetic composition of the invention may also contain one or more cosmetic, dermatological, personal care, or pharmaceutical active agents. The film serves to prevent migration or transfer of the active ingredient by either entrapping the agent within the matrix or forming an adhesive film over the active agent which holds it against the surface.

The invention also relates to a method for therapeutic treatment of the skin. It is further understood that the nanocomposite film of the present invention may be used as a carrier or together with therapeutic agents together with or adjunctive to pharmaceutical compositions including, but not limited to, anti-acne agents, sunscreens, self-tanning ingredients, anti-inflammatory agents, antiseptic agents, anti-bacterials, anti-fungals, anti-virals, anti-yeast agents, eye treatments, age spot treatments, anti-oxidants, moisturizing agents, antiseptic agents, anti-oxidants, moisturizing agents, analgesics, anti-dandruff and antiseborrhetic agents, hyperkeratolytics, antipsoriatic agents, skin lightening agents, depigmenting agents, wound healing agents, burn treatments, tanning agents, hair treatment agents, hair growth products, wart removers, hormones, antipyretics, agents for lupus, multiform erythema, photo allergic and photo toxic reaction and atopic dermatitis or a body personal care composition, such as an antiperspirant or deodorant.

These active agents may be used in amounts usual for a person skilled in the art and especially at concentrations ranging from about 0% to about 20%. Each composition may further comprise, depending on the intended type of application, the constituents conventionally used in the fields under construction which are present in an amount that is suitable for the desired presentation form.

In one embodiment, active ingredients added to the composition may include, but are not limited to, those known for their activity on skin aging, such as ascorbic acid or Vitamin C and derivatives thereof; retinoids such as retinol (Vitamin A) and the esters thereof (palmitate), retinoic acid and the derivatives thereof. Active ingredients may also include chemical sun filters useful in the cosmetic field including any UVA and UVB filter useful in the cosmetic field including mixtures thereof and blends with physical filters. Physical filters include, but are not limited to, titanium, zinc, iron, zirconium, cerium oxides or metal oxides, or mixtures thereof.

The composition may also be directed to a film which acts as a delivery system for the controlled release of cosmetic or pharmaceutical ingredients. For example, the film may provide for encapsulation of ingredients via a population of microstructures comprising a permeable polymer shell where the diffusion characteristics vary with the population of microstructures. It also provides a method of forming a film containing controlled release microstructures under conditions that permit in situ cross-linking of POSS.

Method of Use

A subject of the invention is also the use of a composition as defined above, to obtain a long-lasting, transfer-resistant, breathable and comfortable film, especially a transfer-resistant make-up result, on keratinous material, in particular, on the skin and lips.

The subject of the invention also relates to the cosmetic use of the cosmetic composition defined above to improve the properties of sustainability, transfer-resistance, breathability and comfort of the make-up on keratinous tissue.

In another embodiment, the present invention also relates to a method for making up or caring for mammalian keratinous areas which comprises applying to the keratinous tissue a cosmetic product as defined above, and distributing it homogeneously.

The present invention still further relates to a cosmetic process for making up or caring for keratinous areas, comprising applying to the keratinous tissue a first composition comprising a polymer and a cross-linking agent as described above and then applying onto all or part of the first composition, a second composition comprising graftable POSS dispersed/dissolved in a cosmetic matrix, sequentially applied to form a film in situ thereupon.

The present invention also relates to a cosmetic process for making up or caring for keratinous areas, comprising applying to the keratinous tissue a one-part composition containing functionalized or unfunctionalized polymer with Si—H functionalized POSS mixed with a cross-linking agent which is moisture-activated via application to pre-moistened or applied concurrently with moisture and cures in-situ thereupon.

A person skilled in the art can select the appropriate presentation form, and also the method of preparing it, on the basis of general knowledge, taking into account the nature of the constituents used and the intended use of the composition.

Compositions of the invention can be obtained, for example, according to preparation processes conventionally used in cosmetics or in dermatology. Such processes typically involve mixing of the ingredients in one or more steps to a relatively uniform state, with or without heating, cooling, application of vacuum, and the like.

The compositions herein can be used by topically applying to the areas of the skin a safe and effective amount of the compositions. The effective amount can easily be determined by each user.

As used herein, the term, "safe and effective amount" refers to a sufficient amount of a compound, composition or other material described by this phrase to significantly induce a breathable, elastic, comfortable film, but low enough to avoid undue side effects (e.g., significant skin irritation or sensitization), within the scope of sound judgment of the skilled person. The safe and effective amount of the compound, composition or other material may vary with the particular keratinous material being treated, the age and physical condition of the biological subject being treated, the severity of the skin condition, the duration of treatment, the nature of concurrent therapy, the specific compound, composition, or other material employed, the particular cosmetically acceptable topical carrier utilized, and the factors within the knowledge and expertise of the skilled person.

The composition can be applied for several days, weeks, months or years at any intervals. The compositions are generally applied by light massaging the composition onto the skin. However, the method of application may be any method known in the art and is thus not limited to the aforementioned.

The present invention also applies to a cosmetic kit suitable for application of a film to mammalian keratinous material. The cosmetic kit includes a first composition containing a functionalized polymer and a cross-linking agent; and a second part composition comprising graftable POSS particles, sequentially applied wherein the second part composition is topically applied after the first part composition. The composition of the kit can be accompanied by suitable applicators such as, but not limited to, two-part actuators, double-barrel syringes, tubes, and the like.

The following is a description of a method for manufacturing the POSS based in-situ cross-linking composition of the present invention. The hydrosylilation cross-linking reaction comprises a functionalized polymer, Si—H functionalized POSS, and a catalyst for the hydrosyliation reaction.

A person skilled in the art can select the appropriate presentation form, and also the method of preparing it, on the basis of general knowledge, taking into account the nature of the constituents used and the intended use of the composition.

The composition useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like.

The following examples describe specific aspects of the invention to illustrate the invention and provide a description of the present methods for those skilled in the art. The Examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

EXAMPLES

The following examples illustrate examples of the claimed cosmetic composition of the present invention but are not intended to be limiting thereof.

Example 1

Referring to Table 1, a cross-linkable POSS composition was prepared by mixing the following components: 70 parts by weight of Dow Corning 8-8024 Base, 20 Parts by weight of Dow Corning 0.65 cst fluid, and 10 parts by weight of Pigment Blend. The Dow Corning 8-8024 Base comprises a polydimethylsiloxane polymer having reactive dimethylvinyl end groups and dimethyl, methylhydrogen siloxane. The ingredients were combined together in a beaker and mixed with a propeller mixer until uniform. The blended ingredients were then transferred to individual packages.

The top coat, comprises the curing agent, functionalized POSS which contains platinum catalyst. The Dow 200® Fluid employed in the top coat is a linear PDMS polymer having a high viscosity. The top coat is kept separate from the base coat until application to the lips. To prepare the curing composition, the ingredients were combined together in a beaker, and mixed with a propeller mixer until uniform, and homogenized until the ingredients were fully dispersed. The blended ingredients were then transferred to individual packages.

The base formula is then applied to the lips followed by application of the curing composition.

TABLE 1

| Base Formula | |
|---|---|
| Dow Corning 8-8024 Base | 70 |
| Dow Corning 0.65 cst Fluid | 20 |
| Pigment Blend | 10 |
| Curing Agent Formula | |
| 8% POSS in IDD/penta ne | 60 |
| Dow Corning 0.65 cst | 30 |
| Dow Corning 200 Fluid 100,000 cst* | 10 |

*100,000 cSt available as 200 series fluid from Dow Corning.

Example 2

Transfer Resistance Test

The transfer resistance of the lipstick composition of Example 1 was evaluated in-vitro using the following parameters: oil transfer resistance and water transfer resistance. The parameters were measured according to a modification of the transfer resistance testing protocol of U.S. Pat. No. 6,074,654, the disclosure of which is hereby incorporated by reference. The testing protocol is described below.

The example includes both a positive control and a negative control. The positive control was LipFinity™ (Max Factor), a two-coated product, with a base coat that contains silicone resin and volatile oils and the top coat which contains a sucrose ester. This product is marketed as transfer-resistant lip coloring make-up. A positive control confirmed that the basic conditions of the experiment were able to produce a positive result, even if none of the actual experimental samples produce positive results. The negative control was Lip Polish™ (Maybelline). A negative control demonstrates the base-line result obtained when the test does not produce a measurable positive result (i.e., a background curve).

This method may be utilized to determine the water and oil transfer resistance and adhesion properties of a cosmetic film. This test predicts the ability of a cosmetic film to resist color transfer to objects contacting the skin. Such objects include clothing, handkerchiefs or tissues, napkins and implements such as cups, glasses and table wear, and oily fingers or objects such as oily foods.

Films formed from cosmetic compositions exhibit a degree of transfer resistance directly proportional to the hardness and solvent-resistance of the film. The hardness and solvent-resistance can be expressed as a function of the blot and rub test as described below. Standard safety measures were observed when performing this test.

Equipment:
(1) Glass plates;
(2) Collagen sausage casing such as Nippi Casing F Grade;
(3) Constant humidity chamber adjusted to 95% relative humidity;
(4) Utility knife;
(5) Ruler;
(6) Single-sided adhesive tape;
(7) Double-sided adhesive tape;
(8) 25 micron thickness slot draw-down bar;
(9) White Styrofoam dinner plate such as Amoco Selectables™ Plastic DL® Tableware;
(10) 1.5 inch diameter circular metal punch;
(11) 1 kilogram weight;
(12) Vegetable oil;
(13) Brush-tip cosmetic applicator; and
(14) Lint-Free wiper, such as Kimwipes® EX-L.

Procedure:
(1) A 3×4 inch sheet of collagen sausage casing was prepared by hydrating it in a 90% relative humidity chamber for at least 24 hours.
(2) The collagen sheet was removed to ambient conditions and immediately wrapped tightly around the glass plate. The collagen sheet was attached to the glass using adhesive tape. The collagen surface should be flat and free of wrinkles.
(3) The collagen-wrapped slide was then allowed to equilibrate at ambient conditions for 24 hours.
(4) Thin (1 mm), uniform films of cosmetic were drawn down on the collagen. The base coat was applied first and the top coat was applied immediately thereafter.
(5) The cosmetic samples on the collagen surface were allowed to sit at ambient conditions for one hour.
(6) Using a pipette, three drops of vegetable oil were dropped onto the right side. Using another pipette, three drops of water were dropped onto the left side.
(7) Separately for the oil and water sections, the oil and water were evenly distributed over the film surface with cosmetic brush applicators, brushing lightly.
(8) The oil and water were then allowed to remain on the film undisturbed for 15 minutes.
(9) Using a lint-free wiper, excess oil and water was carefully blotted from the film surface applying as little pressure as possible.
(10) Two disks were cut from a clean, white Styrofoam dinner plate using a 1.5 inch diameter circular punch. The surface and edges of each disk should be smooth and even.
(11) The disks from step (10) were then firmly attached with double-sided adhesive tape to the bottom surface of the 1 kg weight.
(12) The weight was then set on top of the cosmetic sample applied to the collagen surface from step (5) above so that disk #1 was in contact with the oil section of the film. Disk #2 was in contact with the water section of the film. It was important to position the weight gently so that excess force beyond 1 kg was not applied.
(13) Grasping the top of the 1 kg weight, the disk was carefully rotated through 360 degrees while maintaining the 1 kg force on the film. The weight was not lifted or pressed into the film during the rotating motion to the weight. The entire 360 degree rotation was completed within a time interval between 3 and 5 seconds.
(14) The weight was lifted straight up off the film surface and the disk was carefully removed from the weight to avoid damage to the disk.
(15) Color transfer on individual discs was based on visual assessment of the discs compared to commercial products as positive and negative benchmarks. The positive control used was Lipfinity™ (base coat) while negative control used was the Lip Polish™ product.
(16) The criteria used in the "Star Grading System" for measuring the degree of transfer is explained in Table 3 below.

TABLE 2

| Method | Benchmarks |
| --- | --- |
| Transfer Resistance | Lipfinity ™ (Positive control) Lip Polish ™ (Negative control) |

TABLE 3

| Criteria | Scale |
| --- | --- |
| Less than negative control | * |
| Equal to or slight better than negative control | ** |
| Between negative and positive control | *** |
| About equal to positive control | **** |
| Better than positive control | ***** |

The results of the evaluation test are shown in Table 4. Formula POSS-1 represents a one-part composition having a dispersion of nanocomposite POSS comprising 8% by weight of POSS. Formula POSS-2 represents a two-part composition where the first part composition comprises 8% POSS in a base formula and the second part composition is the curing agent formula. The composition has both water and oil transfer resistance better than positive control. The results indicate that the formulations of Example 1 exhibit superior transfer resistance to both the positive (Lipfinity™ base coat) and negative (Lip Polish™) controls.

In each case noticeably less pigment transferred to the Styrofoam disk for the formulation POSS-1 and POSS-2 than for the control products. The results are quantified on the basis of the Star Grading System as shown above in Table 3.

TABLE 4

| Mixing Ratio | POSS-1 | POSS-2 |
| --- | --- | --- |
| 8% POSS | 12.5 | 6.5 |
| Base formula | 87.5 | 87.5 |
| Curing Agent formula | — | 6 |
| Water Transfer Resistance | ***** | ***** |
| Oil Transfer Resistance | ***** | ***** |

Example 3

Flexibility Test

The flexibility of the lip gloss formulation of Examples 1 and 2 was examined using a modification of the flexibility testing protocol described in U.S. Pat. No. 6,074,654, incorporated by reference in its entirety. The flexibility of a cosmetic film is important to both the durability (long-wear) and comfort properties of a cosmetic film.

Flexibility was measured by the latex stretch test. This test predicts the ability of the color film to resist flaking or peeling types of failure after application by movement of the skin during normal activities. The flexibility latex stretch test is based on the weight-loss measurement before and after the latex stretch.

Equipment:
(1) Ansell industrial technicians unlined gloves (12" length, 17 mil) USDA Accepted #390, Size 9;
(2) Slanted eyeshadow brushes from Avon Products, Inc.
(3) Analytical balance (accurate to 4 decimal places); and
(4) Ruler.

Procedure:
(1) A 1 inch wide band was cut from the wrist area of the glove, avoiding the ribbing and thumb.
(2) A 1×1 inch block was marked off in the center of smooth side of the band, avoiding the embossed number.
(3) The weight of the latex band hereinafter referred to as A was taken and recorded.
(4) The initial weight of the cosmetic to be applied to the band in order to produce a dried film weighing 20 mg was determined. This was determined by dividing 20 mg by the weight percent of non-volatile material present in the cosmetic. For example, 40 mg of a cosmetic with 50% non-volatile content must be applied to the band in order to yield a 20 mg dried film.
(5) Using a clean eyeshadow brush, the amount of cosmetic determined in step (4) was evenly applied over the 1×1 inch area of the band as marked in step (2).
(6) The combined weight of the latex band and applied cosmetic was immediately determined. The weight of wet film with the latex band referred to as B was then recorded.
(7) The sample on the latex band from step (6) was allowed to sit at ambient room conditions for one hour.
(8) The combined weight of the latex band A and the applied cosmetic film was determined; hereinafter referred to as C. A was subtracted from C to determine the dried film weight D (D=C−A). This weight was 20±2 mg.
(9) The latex band was gently stretched so that the marked film length changes from 1.00 inches to 1.75 inches.
(10) Upon observing loosened film pieces on the latex band, the film pieces were removed from the latex band by vigorously wiping a clean eyeshadow brush across the surface of the film: wiping 10 times in the vertical direction and 10 times in the horizontal direction.
(11) The latex band was then carefully allowed to return to its approximate original shape.
(12) The weight of the latex band (with the remaining cosmetic) was then determined; herein referred to as E.
(13) A "Star Grading System" was used based on percentage weight loss ("PWL") to grade the flexibility of the films as follows:

| Index | |
| --- | --- |
| Weight Loss | Scale |
| 100-50% | * |
| 30-50% | ** |
| 15-30% | *** |
| 5-15% | **** |
| 0-5% | ***** |

The percent weight loss of the cosmetic film was calculated using the following equation:

Percent Weight Loss $(PWL) = [1-(E-A)/(C-A)] \times 100\%$

For some very flexible films, the percentage weight loss may be negligible. Therefore, in some cases, due to some dust transferred from the brush, the PWL value may become negative (weight gain). Steps (1) through (12) were repeated three times for each cosmetic formulation tested. The average of the three PWL values was determined; herein referred to as Average Percent Weight Loss ("APWL"). Low APWL values (i.e., 0-5%) correspond to flexible films having a desirable adhesive and cohesive balance of the film. The results are shown in Table 5.

TABLE 5

| Mixing Ratio | POSS-1 | POSS-2 |
|---|---|---|
| 8% POSS in Pentane | 12.5 | 6.5 |
| Base Formula | 87.5 | 87.5 |
| Curing Agent formula | — | 6 |
| Flexibility | ***** | ***** |

The invention claimed is:

1. A composition for application to mammalian keratinous material able to crosslink in-situ while leaving a film on said mammalian keratinous material, said composition comprising: a first part composition of a polymer and a cross-linking agent, and a second part composition of graftable particle dispersed in a cosmetic matrix, wherein the graftable particle comprises polyhedral oligomeric silsequioxanes ("POSS") having a molecular formula $RSiO_{1.5}$ in an amount from about 0.001% to about 50% by weight of the composition.

2. The composition of claim 1, wherein the cross-linking agent is a catalyst comprising from about $1 \times 10^{-7}$ to about $1 \times 10^{-3}$ parts by weight per 100 parts by weight of the graftable POSS and is selected from the group consisting of a hydrosilylation catalyst and a condensation catalyst.

3. The composition of claim 1, wherein the polymer is nonfunctionalized and the graftable POSS undergoes self cross-linking.

4. The composition of claim 3, where the nonfunctionalized polymer is polydimethyl siloxane ("PDMS") having a viscosity ranging from about 10,000 cSt to about 3,000,000 cSt.

5. The composition of claim 1, wherein the polymer is functionalized with a group selected from vinyl, Si—H, —OH, —OCH3, and —CN and undergoes cross-linking with the graftable POSS.

6. The composition of claim 1, wherein the polymer is present in amounts ranging from about 0.05% to about 50% by weight of the composition.

7. The composition of claim 1 further comprising at least one additional ingredient selected from the group consisting of cosmetic, personal care, dermatological and pharmaceutical active agents.

8. The composition of claim 1, wherein said composition is in the form of a foundation, makeup, lip make-up, eyeliner, insect repellant, mascara, skin lotion, cream, sunscreen composition, skin or hair cleaning shampoo, or conditioner.

9. The composition according to claim 1, wherein the composition is a lip make-up.

10. The composition of claim 1, having a form selected from a liquid, solid, cream, ointment, solution, gel, film, mousse, stick, cream, spray, powder, emulsion, and dispersion.

* * * * *